United States Patent [19]

Harris et al.

[11] 4,066,704
[45] Jan. 3, 1978

[54] CATALYTIC OXIDATION

[75] Inventors: Norman Harris; David Naden, both of Stockton-on-Tees, England

[73] Assignee: The Power-Gas Corporation Limited, Teesside, England

[21] Appl. No.: 102,067

[22] Filed: Dec. 28, 1970

[30] Foreign Application Priority Data

| Mar. 24, 1970 | United Kingdom | 14072/70 |
| July 16, 1970 | United Kingdom | 34508/70 |
| July 20, 1970 | United Kingdom | 35500/70 |
| Oct. 22, 1970 | United Kingdom | 50131/70 |

[51] Int. Cl.$^2$ .................... C07C 45/02; B01J 23/00
[52] U.S. Cl. .................... 260/604 R; 260/346.75; 260/533 N; 260/680 E; 260/683 R; 252/461; 252/467; 252/469; 252/462
[58] Field of Search .............. 260/604 R, 680 E, 677

[56] References Cited

U.S. PATENT DOCUMENTS

| 3,224,195 | 6/1967 | Hwa et al. | 260/680 |
| 3,293,290 | 12/1966 | Flint et al. | 260/604 R |
| 3,427,343 | 2/1969 | Callahan et al. | 260/604 R |

FOREIGN PATENT DOCUMENTS

| 2,000,819 | 9/1969 | France | 260/604 R |
| 1,488,234 | 6/1967 | France | 260/604 R |

OTHER PUBLICATIONS

Shatalova et al., Chemical Abstracts, vol. 69, 86280a, 1968.
Shtern et al., The Gas Phase Oxidation of Hydrocarbons, 1964.

Primary Examiner—Bernard Helfin
Assistant Examiner—G. T. Breitenstein
Attorney, Agent, or Firm—Cushman, Darby & Cushman

[57] ABSTRACT

Alkanes are catalytically oxidized in the absence of ammonia by passing a feed gas including the alkane and oxygen at an elevated temperature over a solid catalyst. The partial pressure of the alkane in the feed gas exceeds 0.70 atmospheres absolute. Examples of the catalytic oxidation are the production of acrolein and methacrolein and acrylic acid and methacrylic acid from propane and iso-butane.

2 Claims, No Drawings

CATALYTIC OXIDATION

This invention relates to the catalytic oxidation, including oxidative dehydrogenation, of cyclic and acyclic alkanes. The invention is applicable for example to oxidative dehydrogenation of alkanes to alkenes and to the oxidation of alkanes to aldehydes and acids. Catalytic oxidation processes carried out in the presence of ammonia, generally referred to as "ammoxidation processes", are specifically excluded from the scope of the invention.

There have been numerous previous proposals for producing acrolein or methacrolein, and acrylic or methacrylic acid by the catalytic oxidation of propylene or iso-butylene, using a feed gas containing a relatively low concentration of alkene. In these proposals, any alkane present has been considered inert and acted merely as a diluent, taking no part in the catalytic reaction. Contrary to the previous findings, the present invention makes possible catalytic oxidation and dehydrogenation of alkanes.

The invention is based on the use of a high partial pressure of the hydrocarbon (i.e., alkane) vapour in the feed gas to the catalytic reaction, compared with that commonly used in the corresponding alkene reaction; by so doing the required product is produced in the exit gases in proportions that are sufficiently high to render its extraction possible on a commercial scale, even at a relatively low figure of reaction conversion (defined as the difference in the amounts of the alkane in the feed gas and in the exit gas divided by the amount of the alkane in the feed gas).

The present invention resides in a process for the catalytic oxidation, including oxidative dehydrogenation, of an alkane, in which a feed gas comprising the alkane in vapour phase is passed at an elevated temperature over a suitable solid catalyst, and in which the partial pressure of the alkane in the feed gas is in excess of 0.70 atmospheres absolute. The alkane may have no more than 20 carbon atoms and preferably contains between three and eight carbon atoms.

The catalyst is normally constituted by the oxides of selected elements. It is possible to operate using a feed gas not containing oxygen, the catalyst being regenerated either by frequently interrupting the supply of feed gas and substituting a regenerating gas stream containing oxygen, or by circulating the catalyst through a separate regeneration stage. However it is preferred to operate with a feed gas containing the alkane and oxygen, when such regeneration of the catalyst becomes unnecessary.

The alkane preferably constitutes at least 70% of the feed gas by volume and is operated at a pressure not significantly higher than atmospheric.

The catalyst is chosen according to a number of factors, among which is the conversion. It is preferred to select the catalyst and operating conditions to achieve a high productivity of the desired product at relatively low reaction conversion.

The active constituents of the catalyst composition preferably consist essentially of the oxides of the two, three or more selected metals or of a stoichiometric or non-stoichiometric compound of the said metals and oxygen.

The mixed oxide catalysts may be prepared by mixing together the appropriate oxides in finely divided form. However, the preparation is most conveniently accomplished by mixing the oxides, hydroxides or hydrated oxides in aqueous suspension and evaporating the resulting mixture to dryness or filtering off the suspended solid. Such aqueous suspensions may be prepared in a number of convenient ways; for example, in the cases of antimony and tin, the metal may be oxidised with concentrated nitric acid, whereas in the cases of vanadium, molybdenum or uranium, a solution of a salt, e.g. ammonium metavanadate, ammonium paramolybdate or uranyl nitrate respectively may be hydrolysed.

When the suspension has been evaporated to dryness or filtered, the mixed oxide product is preferably subjected to a further heat treatment (hereinafter referred to as calcining) in order to facilitate the production of a reproducible catalyst. The calcining may be performed in air, over the temperature range 300° to 950° C. Since the final oxidation state of the mixed oxide catalyst composition (which may be stoichiometric or non-stoichiometric) and its crystal and phase structure is largely determined by the final calcining, it will be appreciated that it is possible to use as starting materials oxides and other appropriate compounds of the metals in question in which the metals are in valency states other than those in which they are present in the final composition. For example, tri- or penta-valent compounds of antimony may be used or tetra- or penta-valent compounds of vanadium. In order to promote reproducibility of catalyst, it is preferred that the final calcining is carried out for at least 4 hours.

The ratio of the metallic elements in the catalyst composition may vary over a considerable range, the optimum ratio depending upon the elements involved and the operating conditions under which the catalyst is to be used. However, this ratio may be readily established by experiment. For example, in the case of catalysts containing binary mixtures of vanadium and antimony, the atomic ratio of vanadium and antimony is conveniently from 0.05 to 1.5, but is preferably from 0.1 to 0.7.

The catalyst is preferably used in the form of particles to facilitate gas/solid contact in the reactor. Within the term "particles" we wish to include powders, granules, pellets and the like. The particles may consist of the catalyst material alone; or may be mixed with particles of an inert and refractory material, which may if desired be present as the major constituent of the solid catalyst. Alternatively the catalyst material may be applied as a layer on the surface of an inert support.

The process is preferably operated on a continuous basis, with mean gas feed-catalyst contact times from 0.01 to 10 seconds, particularly from 0.1 to 3 seconds. By "contact time" we means a figure, in seconds, obtained by dividing the bulk volume of catalyst by the volumetric gas flow per second, measured under ambient conditions.

The reactor may be of the fluidised, moving or static bed type and the catalytic ammoxidation reaction may be arranged to take place isothermally or adiabatically. Preferably the required product or products is removed from the exit gases along with waste products such as carbon dioxide and the remaining gases constituted primarily by unconverted alkane and oxygen, are mixed with appropriate quantities of fresh reactant gases and recycled to the inlet of the reactor.

Among the oxidation and oxidative dehydrogenation processes envisaged in this invention are:
   a. the dehydrogenation of alkanes to mono- or polyunsaturated hydrocarbons, e.g. alkenes or dienes, and particularly of propane to propylene, of isobutane to iso-butylene, of n-butane to butenes and/or butadiene and of iso-pentane to iso-pentene and/or isoprene.

b. the oxidation of alkanes to aldehydes, and particularly of propane to acrolein, of iso-butane to methacrolein, and of n-butane to crotonaldehyde or acetaldehyde.

c. the oxidation of alkanes to acids, and particularly of propane to acrylic acid, of iso-butane to methacrylic acid, and of n-butane to maleic acid or acetic acid, and d. the oxidation of n-butane to maleic anhydride.

The product obtained in any one instance will depend on the alkane supplied, the reaction conditions and the catalyst used. It is possible in some circumstances to obtain a mixture containing two or more desired products.

When the alkane is oxidised to an aldehyde, the catalyst preferably comprises one of the elements Sb, Mo, W, V and Bi; at least one other of those elements, and/or at least one of the elements Fe, Sn, U, Ti, Pb, Co, Cu and P; and oxygen.

When the alkane is dehydrogenated to an alkene or diene, the catalyst preferably comprises at least two of the elements V, Sb, Cr, Fe, Mo, Sn, Co, Cu, Pb, Bi, U, Ti, W, Ce and As, and oxygen.

The invention includes an oxidation catalyst which can be used in the oxidation/dehydrogenation of alkanes having from three to eight carbon atoms per molecule, and which comprises the oxides of at least the elements of one of the pairs Ti/V,Sb/Ti, Sb/Pb or a compound including one of those pairs of elements and oxygen.

The invention will be more readily understood by way of example from the following Examples:

CATALYST PREPARATION

Each catalyst employed with the following examples was prepared as follows:

Where possible, the finely divided, freshly prepared, oxide, hydroxide or insoluble acid of each element forming the catalyst was prepared separately. Then, the compounds of the two or more elements of the catalyst were mixed in the aqueous phase at 30°–100° C for a number of hours, allowed to cool to room temperature and filtered the recovered solid mixture was dried in air at 110° C for 16 hours, and finally pelletted, and calcined at the calcinatim temperatures specified in the examples.

In those cases, where it was not possible to prepare solid oxides or hydroxides, a soluble salt or acid of one of the catalyst constituents was mixed with the oxide, hydroxide or soluble salt or acid of the other constituent or constituents, evaporated to dryness, pelleted and calcined at the stipulated temperature.

EXAMPLE 1

Butane Oxidation to Maleic Anhydride

The catalyst in this case had the following composition of active components, the proportions being given in mole percent:

Tungstic Oxide: 77.3
Vanadium Pentoxide: 18.2
Phosphorus Pentoxide: 4.5

The catalyst had a volume of 25 cc and a bulk density of 2.10 grammes/cc. Calcination was effected at 450° C for 24 hours.

Butane feed gases of various compositions were passed over the catalyst to produce maleic anhydride in the exit gases. The compositions, reaction conditions and results are given in the following table:

| Feed gas composition | | | | |
|---|---|---|---|---|
| Vol. % n $C_4H_{10}$ | 79.5 | 78.0 | 4.9 | 2.5 |
| i $C_4H_{10}$ | 0.2 | 0.2 | <0.02 | <0.02 |
| $O_2$ | 20.3 | 21.8 | 20.1 | 20.6 |
| $N_2$ | <0.1 | <0.1 | 74.9 | 76.8 |
| Reaction temperature ° C | 350 | 356 | 352 | 399 |
| Flow rate of reactants l/h | 104.4 | 206.3 | 109.1 | 102.3 |
| Moles product/100 moles butane feed | | | | |
| Maleic anhydride | 0.33 | 0.18 | 0.17 | 0.28 |
| Useful oxidation products | 1.29 | 0.64 | 1.30 | 3.55 |
| Oxides of carbon | 1.78 | 1.32 | 2.56 | <3.3 |
| Space time yield of Maleic anhydride Moles/liter catalyst/hr | 0.492 | 0.528 | 0.016 | 0.012 |

The useful oxidation products are organic acids and aldehydes.

EXAMPLE II

Butane Oxidation to Maleic Anhydride

The catalyst consisted of 50% by weight of vanadium pentoxide and 50% by weight of phosphorus pentoxide, and had a volume of 25 cc and a bulk density of 0.52 grammes/cc. Calcination was effected at 450° C for 240 hours.

Butane feed gases of various compositions were passed over the catalyst to produce maleic anhydride in the exit gases. The compositions, reaction conditions and results are given in the following table

| Feed gas composition | | | | |
|---|---|---|---|---|
| Vol. % n $C_4H_{10}$ | 79.8 | 79.2 | 2.84 | 3.0 |
| i $C_4H_{10}$ | 0.2 | 0.2 | <0.02 | <0.02 |
| $O_2$ | 20.0 | 20.6 | <20.5 | 20.5 |
| $N_2$ | <0.1 | <0.1 | 76.5 | 76.5 |
| Reaction temperature ° C | | 394 | 425 | 424 | 500 |
| Flow rate of reactants l/h | | 103.0 | 99.4 | 105.3 | 101.9 |
| Moles product/100 moles of butane feed | | | | |
| Maleic anhydride | 0.16 | 0.75 | 1.05 | 4.28 |
| Useful oxidation products | 0.43 | 2.86 | 4.05 | 10.75 |
| Oxides of carbon | 0.12 | 3.24 | 6.90 | 22.88 |

Space Time Yield of Maleic Anhydride

Moles/liter catalyst/hr 0.240 1.060 0.056 0.236 In the following examples 3 and 4, isobutane is converted to methaerolein by passing a feed gas of isobutane, oxygen and nitrogen through a reactor Examples 3 and 4 include, by way of comparison, the results obtained by passing a lean hydrocarbon feed gas through the reactor under the same conditions.

EXAMPLE 3

The catalyst consisted of bismuth-molybdenum oxide with a Bi/Mo atomic ratio of 2/1, and had a volume of 25 ml. and a bulk density of 2.11. Calcination was at a temperature of 500° C for 16 hours.

| Feed gas composition % | Example | | | Comparison Example | | |
|---|---|---|---|---|---|---|
| i $C_4H_{10}$ | | | 80 | | | 4 |
| $N_2$ | | | <0.1 | | | 76 |
| $O_2$ | | | 20 | | | 20 |
| Reactor Temperature (° C) | 450 | 500 | 530 | 450 | 500 | 530 |
| Volume flow rate of reactants l/h | 100 | 100 | 200 | 100 | 100 | 100 |
| % composition of outlet gas | | | | | | |
| oxides of carbon | 0.44 | 2.01 | 0.79 | 0.02 | 0.02 | 0.01 |
| isobutylene | <0.02 | <0.02 | <0.02 | <0.02 | <0.02 | <0.02 |
| acrolein | <0.02 | 0.08 | 0.12 | <0.02 | <0.02 | <0.02 |
| methacrolein | 0.23 | 0.61 | 0.43 | 0.02 | 0.02 | 0.03 |
| Methacrolein STY) moles/liter) catalyst/hr) | 0.41 | 1.07 | 1.59 | 0.05 | 0.04 | 0.06 |

EXAMPLE 4

The catalyst consisted of antimony-molybdenum oxide with a Sb/Mo atomic ratio of 1/1, and had a volume of 25 ml. and a bulk density of 1.54. Calcination was at a temperature of 550° C for 4½ hours.

| Feed gas composition % | Example | | | Comparison Example | | |
|---|---|---|---|---|---|---|
| i $C_4H_{10}$ | | | 80 | | | 7.5 |
| $N_2$ | | | <0.1 | | | 73.0 |
| $O_2$ | | | 20 | | | 19.5 |
| Reactor Temperature (°) | 450 | 500 | 530 | 450 | 500 | 530 |
| Volume flow rate of reactants l/h | 100 | 100 | 100 | 100 | 100 | 100 |
| % composition of outlet gas | | | | | | |
| oxides of carbon | 0.86 | 3.31 | 4.76 | 0.17 | 0.53 | 0.77 |
| isobutylene | 0.61 | 0.95 | 1.16 | <0.02 | <0.02 | <0.02 |
| acrolein | <0.02 | 0.02 | 0.06 | <0.02 | <0.02 | <0.02 |
| methacrolein | 0.60 | 1.56 | 2.17 | 0.05 | 0.12 | 0.18 |
| Methacrolein STY) moles/liter catalyst/hr) | 1.01 | 2.69 | 3.95 | 0.09 | 0.22 | 0.33 |

EXAMPLES 5 – 25

The following Examples are also concerned with the oxidation of isobutane to methacrolein, using a feed gas of which the proportion by volume of oxygen is stated, the remainder of the feed gas consisting almost exclusively of isobutane, and using further catalysts:

| Ex. | Catalyst Composition (as oxides) | Atomic Ratio | Calcination Temp ° C | hrs. | Vol. used ml. | Bulk Density gm/ml | Reaction Temp. ° C | Pressure atmos. | Feed Flow l/h | % $O_2$ in feed gas | % methacrolein in product gas | Methacrolein Space time yield moles/liter catalyst/hour |
|---|---|---|---|---|---|---|---|---|---|---|---|---|
| 5 | Sb/V | 9/1 | 650 | 8 | 25 | 1.46 | 452 | 1.1 | 109 | 20.0 | 0.90 | 1.8 |
| | | | | 10 | | | 507 | 1.5 | 100 | 19.9 | 1.4 | 6.2 |
| | | | | 10 | | | 548 | 1.5 | 96 | 19.8 | 1.7 | 7.3 |
| 6 | Sb/W | 1/1 | 550 | 4 | 25 | 1.06 | 440 | 1.1 | 106 | 21.7 | 0.29 | 0.6 |
| | | | | | | | 506 | 1.1 | 109 | 21.1 | 0.86 | 1.7 |
| | | | | | | | 543 | 1.1 | 108 | 19.9 | 1.3 | 2.5 |
| 7 | Co/Mo | 1/1 | 550 | 4 | 10 | 0.82 | 443 | 1.2 | 106 | 20.2 | 0.22 | 1.0 |
| | | | | | | | 497 | 1.3 | 107 | 20.7 | 0.75 | 3.6 |
| 8 | Sb/Fe | 1/1 | 650 | 8 | 10 | 1.6 | 447 | 1.3 | 88 | 20.5 | 0.21 | 0.8 |
| | | | | | | | 469 | 1.3 | 85 | 20.5 | 0.24 | 0.9 |
| 9 | Sb/Mo | 2/1 | 550 | 4 | 25 | 1.40 | 450 | 1.1 | 110 | 15.4 | 0.11 | 0.22 |
| | | | | | | | 502 | 1.1 | 112 | 15.6 | 0.62 | 1.2 |
| | | | | | | | 499 | 2.0 | 186 | 15.2 | 1.0 | 3.3 |
| 10 | Sb/Sn | 9/1 | 550 | 4 | 10 | 1.79 | 449 | 1.2 | 103 | 21.1 | 0.16 | 0.7 |
| | | | | | | | 498 | 1.3 | 105 | 20.5 | 0.38 | 1.8 |
| | | | | | | | 554 | 1.3 | 103 | 21.3 | 1.29 | 5.9 |
| 11 | Cu/Mo | 1/1 | 550 | 4 | 10 | 1.11 | 428 | 1.3 | 138 | 19.1 | 0.19 | 1.2 |
| | | | | | | | 484 | 1.2 | 118 | 19.6 | 0.40 | 2.1 |
| | | | | | | | 528 | 1.3 | 119 | 19.4 | 0.76 | 4.0 |
| 12 | Pb/Mo | 1/1 | 550 | 4 | 10 | 2.50 | 437 | 1.37 | 162 | 19.8 | 0.18 | 1.30 |
| | | | | | | | 485 | 1.41 | 119 | 19.2 | 0.57 | 3.02 |
| | | | | | | | 531 | 1.41 | 116 | 20.6 | 1.29 | 6.70 |
| 13 | Sb/U | 1/1 | 530 | 4 | 10 | 1.58 | 491 | 1.21 | 109 | 20.5 | 0.17 | 0.83 |
| | | | | | | | 540 | 1.21 | 100 | 20.5 | 0.53 | 2.37 |
| 14 | P/V | 1/1 | 450 | 24 | 10 | 0.49 | 442 | 1.17 | 114 | 21.1 | 0.44 | 2.24 |
| | | | | | | | 495 | 1.18 | 112 | 20.9 | 1.09 | 5.44 |
| 15 | Bi/W | 1/1 | 550 | 4 | 10 | 1.69 | 436 | 1.19 | 110 | 21.1 | 0.22 | 1.08 |
| | | | | | | | 495 | 1.22 | 109 | 21.4 | 0.28 | 1.36 |
| | | | | | | | 543 | 1.23 | 107 | 21.4 | 0.39 | 1.85 |
| 16 | Sb/Ti | 1/1 | 550 | 4 | 10 | 1.6 | 448 | 1.24 | 115.2 | 19.7 | 0.13 | 0.67 |
| | | | | | | | 495 | 1.25 | 106.0 | 20.7 | 0.32 | 1.51 |
| | | | | | | | 555 | 1.27 | 108.0 | 22.4 | 0.97 | 4.68 |
| 17 | Sn/Mo | 1/2 | 680 | 5 | 5 | 1.16 | 336 | 1.21 | 102.2 | 8.5 | 0.10 | 0.91 |
| | | | | | | | 374 | 1.22 | 103.8 | 7.9 | 0.28 | 2.59 |
| | Sn/Mo | 1/9 | 550 | 4 | 10 | 1.0 | 397 | 1.24 | 115.9 | 22.9 | 0.31 | 1.60 |

-continued

| Ex. | Catalyst Composition (as oxides) | Atomic Ratio | Calcination Temp °C | hrs. | Vol. used ml. | Bulk Density gm/ml | Reaction Temp. °C | Pressure atmos. | Feed Flow l/h | % O₂ in feed gas | % methacrolein in product gas | Methacrolein Space time yield moles/liter catalyst/hour |
|---|---|---|---|---|---|---|---|---|---|---|---|---|
| 18 | Fe/Mo | 1/1 | 680 | 4 | 10 | 1.41 | 461 | 1.26 | 118.8 | 7.7 | 0.60 | 3.18 |
|    |       |     |     |   |    |      | 426 | 1.12 | 105.6 | 20.8 | 0.07 | 0.33 |
|    |       |     |     |   |    |      | 494 | 1.13 | 117.7 | 20.3 | 0.34 | 1.79 |
|    |       |     |     |   |    |      | 526 | 1.13 | 106.9 | 20.5 | 0.49 | 2.34 |
| 19 | Sb/Pb | 2/1 | 540 | 4 | 10 | 2.38 | 547 | 1.15 | 114.5 | 21.1 | 0.23 | 1.18 |
|    |       |     |     |   |    |      | 569 | 1.16 | 116.8 | 21.1 | 0.32 | 1.67 |
| 20 | Bi/V  | 7/3 | 650 | 8 | 10 | 2.50 | 450 | 1.31 | 110.9 | 22.1 | 0.27 | 1.34 |
|    |       |     |     |   |    |      | 495 | 1.33 | 100.6 | 20.6 | 0.49 | 2.20 |
|    |       |     |     |   |    |      | 525 | 1.35 | 106.5 | 22.1 | 0.69 | 3.28 |
| 21 | V/Mo  | 1/4 | 550 | 5 | 10 | 0.93 | 442 | 1.31 | 101.5 | 20.5 | 0.19 | 0.86 |
|    |       |     |     |   |    |      | 479 | 1.32 | 104.4 | 20.8 | 0.71 | 3.31 |
|    |       |     |     |   |    |      | 544 | 1.43 | 96.6  | 20.4 | 0.98 | 4.22 |
| 22 | V/W   | 1/4 | 550 | 5 | 10 | 1.71 | 398 | 1.33 | 101.5 | 21.0 | 0.29 | 1.31 |
|    |       |     |     |   |    |      | 480 | 1.43 | 98.6  | 7.7  | 0.36 | 1.58 |
| 23 | Sb/Co | 1/1 | 700 | 4 | 10 | 1.24 | 436 | 1.30 | 79.3  | 7.9  | 0.21 | 0.74 |
|    |       |     |     |   |    |      | 482 | 1.33 | 92.6  | 7.8  | 0.30 | 1.24 |
|    |       |     |     |   |    |      | 527 | 1.36 | 96.8  | 7.8  | 0.31 | 1.34 |
| 24 | Ti/V  | 4/1 | 700 | 3 | 10 | 1.82 | 452 | 1.23 | 110.7 | 8.4  | 0.14 | 0.67 |
| 25 | Sn/W  | 1/1 | 550 | 5 | 10 | 2.14 | 435 | 1.26 | approx 100 | 7.5 | 0.15 | 0.8 |
|    |       |     |     |   |    |      | 476 | 1.30 |       | 7.5 | 0.25 | 1.1 |
|    |       |     |     |   |    |      | 520 | 1.30 |       | 7.4 | 0.30 | 1.3 |

EXAMPLE 26

(Conversion of Propane to Propylene)

A catalyst composition was made consisting of 70.6% by weight of vanadium oxide and 29.6% by weight of chromium oxide. The volume of the catalyst was 20 cc and its bulk density 1.6 grammes/cc. Calcination was effected at 750° C for 8 hours.

A gas feed (Composition 1) having a high propane content, and, for comparison, a lean propane gas feed (Composition 2) of otherwise similar composition were prepared with the following compositions by volume:

|  | Composition 1 | Composition 2 |
|---|---|---|
| $C_3H_8$ | 80% | 5% |
| $O_2$ | 10% | 10% |
| $N_2$ | 10% | 85% | and were passed over the catalyst independently at various flow rates and at various temperatures. For each flow rate and for each temperature, the proportion of propylene in the exit gas was measured. The results obtained were as follows, the temperature giving optimum propylene from Composition 1 at each flow rate being given:

| Flow rate (liters/hr) | Temperature °C | % Propylene in exit gas | |
|---|---|---|---|
|   |   | Composition 1 | Composition 2 |
| 48  | 420 | 6.8 | 0.4 |
| 96  | 470 | 7.5 | 0.5 |
| 144 | 490 | 7.2 | 0.5 |

In the following Examples 27 to 36, a feed gas consisting of 80% by volume of propane, 10% by volume of oxygen and the balance of inert constituents was passed through a reactor at a gas rate of 96 liters per hour and the stipulated temperatures over a catalyst having a crushed volume of 20 mls:

| Example | Catalyst Constituents | Molar composition of catalyst | Calcination Temp °C | Hrs. | Reactor Temp °C | % propylene in exit gas |
|---|---|---|---|---|---|---|
| 27 | Antimony oxide/ vanadium oxide | 30:70 | 650 | 8 | 390 | 3.7 |
| 28 | Antimony oxide/ Iron oxide | 70:30 | 650 | 8 | 490 | 2.4 |
| 29 | Molybdenum oxide/ Tin oxide | 90:10 | 650 | 8 | 480 | 2.0 |
| 30 | Antimony oxide/ Molybdenum oxide | 50:50 | 650 | 8 | 490 | 1.7 |
| 31 | Antimony/oxide Tin oxide | 30:70 | 650 | 8 | 440 | 1.1 |
| 32 | Bismuth oxide/ Molybdenum oxide | 10:90 | 500 | 16 | 500 | 0.6 |
| 33 | Molybdenum oxide/ Iron oxide | 30:70 | 680 | 4 | 480 | 3.5 |
| 34 | Vanadium oxide/ Tin oxide | 10:90 | 650 | 8 | 390 | 3.9 |
| 35 | Vanadium oxide/ Bismuth oxide | 90:10 | 650 | 8 | 410 | 2.6 |
| 36 | Antimony oxide/ Uranium oxide | 25:75 | 650 | 8 | 500 | 1.4 |

Conversion of Isobutane to Isobutylene

In each of the following examples, the feed gas consisted of 20% v/v $O_2$ and 80% v/v i—$C_4H_{10}$. The reaction was carried out at atmospheric pressure. The catalyst employed, the reaction conditions and the percentage of isobutylene in the product gas are given in the following table:

| Example | Catalyst Composition (as oxides) | Atomic Ratio | Calcination Temp. °C | hrs. | Catalyst Bulk Density gm/ml. | Mean Reactor Temperature °C | Feed Gas Space Velocity hr$^{-1}$ | % Iso-butylene in Product Gas | |
|---|---|---|---|---|---|---|---|---|---|
| 37 | Sb/V | 9/1 | 650 | 8 | 1.46 | 452 | 4,360 | 1.3 | |
|   |   |   |   |   |   | 507 | 9,960 | 2.8 | |
|   |   |   |   |   |   | 548 | 9,620 | 5.4 | |
| 38 | Co/Mo | 1/1 | 550 | 4 | 0.82 | 443 | 10,560 | 1.5 | |
|   |   |   |   |   |   | 497 | 10,700 | 2.4 | |
| 39 | Sb/Mo | 2/1 | 550 | 4 | 1.40 | 502 | 4,480 | 1.0 | O$_2$ in Feed Gas approx. 16% |
| 40 | Cu/Mo | 1/1 | 550 | 4 | 1.1 | 528 | 11,920 | 0.5 | |
| 41 | Pb/Mo | 1/1 | 550 | 4 | 2.81 | 502 | 11,565 | 0.5 | |
|   |   |   |   |   |   | 539 | 11,454 | 1.8 | |
|   |   |   |   |   |   | 579 | 11,095 | 1.9 | |

In the following examples, concerned again with the oxidative dehydrogenation of iso-butane to isobutylene, the proportion by volume of oxygen is as stated, the balance being constituted almost exclusively by iso-butane.

| Example | Catalyst Composition (as oxides) | Atomic Ratio | Calcination Temp °C | hrs. | Catalyst Bulk Density gm/ml. | Mean Reactor Temperature °C | % O$_2$ in feed | Feed Gas Space Velocity hr$^{-1}$ | % Iso-butylene in product gas |
|---|---|---|---|---|---|---|---|---|---|
| 42 | Sb/Ti | 1/1 | 550 | 4 | 1.6 | 448 | 20 | 11,500 | 0.8 |
|   |   |   |   |   |   | 495 | 21 | 10,600 | 1.4 |
|   |   |   |   |   |   | 555 | 22 | 10,800 | 3.6 |
| 43 | Pb/Mo | 2/1 | 550 | 4 | 2.58 | 498 | 20 | 11,600 | 1.4 |
|   |   |   |   |   |   | 552 | 21 | 11,700 | 3.3 |
| 44 | Sb/Pb | 2/1 | 550 | 7 | 2.38 | 547 | 21 | 11,500 | 2.2 |
|   |   |   |   |   |   | 569 | 21 | 11,700 | 3.9 |
| 45 | Fe/Mo | 1/1 | 680 | 4 | 1.41 | 494 | 20 | 11,800 | 0.6 |
|   |   |   |   |   |   | 526 | 21 | 10,700 | 1.3 |
| 46 | Sn/Mo | 1/9 | 550 | 4 | 1.00 | 442 | 8 | 11,000 | 0.6 |
| 47 | Bi/V | 7/3 | 650 | 8 | 2.50 | 495 | 21 | 10,000 | 0.6 |
|   |   |   |   |   |   | 525 | 22 | 11,000 | 0.7 |
| 48 | V/Mo | 1/4 | 550 | 5 | 0.93 | 479 | 21 | 10,000 | 0.7 |
|   |   |   |   |   |   | 544 | 20 | 10,000 | 1.3 |
| 49 | Ti/V | 4/1 | 700 | 3 | 1.82 | 452 | 8.4 | 11,070 | 0.9 |
| 50 | Sn/W | 1/1 | 550 | 5 | 2.14 | 435 | 7.5 | Approx. 9,900 | 1.0 |
|   |   |   |   |   |   | 476 | 7.5 |  | 1.2 |
|   |   |   |   |   |   | 520 | 7.5 |  | 1.4 |
| 51 | Sb/Co | 1/1 | 700 | 4 | 1.24 | 436 | 7.8 | 7,935 | 0.52 |
|   |   |   |   |   |   | 482 | 7.8 | 9,257 | 0.81 |
|   |   |   |   |   |   | 527 | 7.8 | 9,683 | 1.20 |
| 52 | V/W | 1/4 | 700 | 4 | 1.71 | 432 | 7.7 | 9,191 | 0.46 |
|   |   |   |   |   |   | 480 | 7.7 | 9,860 | 0.50 |

The following Table (Examples 53 to 58) give the catalyst and reaction details and the results obtained, of the oxidation of n-butane to acetic acid and acetaldehyde, using six different catalysts. In each example, the percentage oxygen in the feed gas is given, the balance being made up of n-butane.

| Example | Catalyst Composition (as oxides) | Atomic Ratio | Calcination Temp °C | hrs. | Vol. used ml. | Reaciton Temperature °C | Product Gas Flow 1/hr | % O$_2$ in Feed Gas | Moles Acetic Acid/100 Moles Butane in Feed Gas | Moles Aldehyde 100 Moles Butane in Feed |
|---|---|---|---|---|---|---|---|---|---|---|
| 53 | Sb/V | 70/30 | 750 | 8 | 20 | 371 | 92.1 | 26.0 | 0.06 | 3.4 |
| 54 | Sb/V | 50/50 | 750 | 8 | 25 | 391 | 92.3 | 21.8 | 0.53 | 0.52 |
| 55 | W/V/P | 17/4/2 | 450 | 24 | 25 | 352 | 98.2 | 20.3 | 0.56 | 0.41 |
|   |   |   |   |   |   | 356 | 192.6 | 21.8 | 0.31 | 0.15 |
| 56 | W/V/P 50% TiO$_2$ 50% | 17/4/2 | 450 | 24 | 25 | 363 | 92.6 | 20.3 | 0.98 | 0.68 |
| 57 | P/V | 50/50 | 450 | 24 | 25 | 425 | 88.0 | 20.6 | 0.76 | 1.34 |
| 58 | P/V | 70/30 | 450 | 24 | 25 | 404 | 65.7 | 8.2 | 0.45 | 0.31 |

We claim:

1. A process for the catalytic oxidation or oxidative dehydrogenation of an alkane of 3 to 8 carbon atoms to an aldehyde, in which a feed gas comprising oxygen and the alkane in vapor phase is passed in the absence of ammonia and at a temperature in the range of 350° to 569° C. over a solid oxidation catalyst comprising one of the elements Sb, Mo, W, V and Bi; at least one other of those elements and/or at least one of the elements Fe, Sn, U, Ti, Pb, Co, Cu and P; and oxygen, and in which the partial pressure of the alkane in the feed gas is in excess of 0.70 atmosphere absolute and the alkane constitutes more than 70% of the feed gas by volume.

2. A process according to claim 1 in which the alkane and oxygen constitute approximately 80% and 20% respectively of the feed gas by volume.

* * * * *